United States Patent
Gonzales et al.

(10) Patent No.: US 8,753,255 B2
(45) Date of Patent: *Jun. 17, 2014

(54) METHODS AND COMPOSITIONS FOR TREATING LUMINAL INFLAMMATORY DISEASE

(75) Inventors: Gilbert R. Gonzales, New York, NY (US); Nicolas Chronos, Atlanta, GA (US)

(73) Assignee: Clear Vascular Inc., New York, NY (US)

(*) Notice: Subject to any disclaimer, the term of this patent is extended or adjusted under 35 U.S.C. 154(b) by 27 days.

This patent is subject to a terminal disclaimer.

(21) Appl. No.: 12/963,508

(22) Filed: Dec. 8, 2010

(65) Prior Publication Data

US 2011/0077211 A1  Mar. 31, 2011

Related U.S. Application Data

(63) Continuation of application No. 11/428,823, filed on Jul. 5, 2006, now Pat. No. 7,874,975.

(60) Provisional application No. 60/701,371, filed on Jul. 20, 2005.

(51) Int. Cl.
*A61N 5/00* (2006.01)

(52) U.S. Cl.
USPC ............................................ 600/4; 600/3

(58) Field of Classification Search
USPC .................... 600/1–8; 424/1.11, 1.69, 9.6
See application file for complete search history.

(56) References Cited

U.S. PATENT DOCUMENTS

| | | | |
|---|---|---|---|
| 6,517,810 B1 * | 2/2003 | Srivastava et al. | 424/1.65 |
| 7,874,975 B2 * | 1/2011 | Gonzales et al. | 600/4 |
| 2003/0152513 A1 * | 8/2003 | Blankenberg et al. | 424/1.49 |

OTHER PUBLICATIONS

Qaim et al. (Int. J. Appl. Radiat. Isot. 1984, 35, 645-650).
Mausner et al. (Radiation Effects 1986, 94, 59-63).

* cited by examiner

*Primary Examiner* — Christine Matthews
(74) *Attorney, Agent, or Firm* — Wood, Herron & Evans, LLP

(57) ABSTRACT

Compositions, articles, and methods for treating and imaging vulnerable plaque and other inflamed regions in a patient rely on delivery of a conversion electron emitting source (CEES) to a body location. The CEES may be delivered by coupling to a substance which preferentially binds to vulnerable plaque or other inflammatory marker. Alternatively, the CEES can be delivered on a catheter, scaffold, or other device.

5 Claims, No Drawings

METHODS AND COMPOSITIONS FOR TREATING LUMINAL INFLAMMATORY DISEASE

CROSS-REFERENCES TO RELATED APPLICATIONS

The present application is a continuation of U.S. patent application Ser. No. 11/428,823, filed Jul. 5, 2006, which claims priority from U.S. Provisional Patent Application No. 60/701,371, filed Jul. 20, 2005, the full disclosures of which are incorporated herein by reference.

BACKGROUND OF THE INVENTION

1. Field of the Invention

The present invention relates generally to medical methods and compositions. More particularly, the present invention relates to methods and compositions for treating and imaging regions of inflammation in body lumens such as vulnerable plaque in the vasculature.

Coronary artery disease resulting from the build-up of atherosclerotic plaque in the coronary arteries is a leading cause of death in the United States and worldwide. The plaque build-up causes a narrowing of the artery, commonly referred to as a lesion, which reduces blood flow to the myocardium (heart muscle tissue). Myocardial infarction (better known as a heart attack) can occur when an arterial lesion abruptly closes the vessel, causing complete cessation of blood flow to portions of the myocardium. Even if abrupt closure does not occur, blood flow may decrease resulting in chronically insufficient blood flow which can cause significant tissue damage over time.

A variety of interventions have been proposed to treat coronary artery disease. For disseminated disease, the most effective treatment is usually coronary artery bypass grafting where problematic lesions in the coronary arteries are bypassed using external grafts. In cases of less severe disease, pharmaceutical treatment is often sufficient. Finally, focal disease can often be treated intravascularly using a variety of catheter-based approaches, such as balloon angioplasty, atherectomy, radiation treatment, stenting, and often combinations of these approaches.

With the variety of treatment techniques which are available, the cardiologist is faced with a challenge of selecting the particular treatment which is best suited for an individual patient. While numerous of diagnostic aids have been developed, no one technique provides all the information which is needed to select a treatment. Angiography is very effective in locating lesions in the coronary vasculature, but provides little information concerning the nature of the lesion. To provide better characterization of the lesion(s), a variety of imaging techniques have been developed for providing a more detailed view of the lesion, including intravascular ultrasound (IVUS), angioscopy, laser spectroscopy, computed tomography (CT), magnetic resonance imaging (MRI), and the like. None of these techniques, however, is completely successful in determining the exact nature of the lesion. In particular, such techniques provide little information regarding whether the plaque is stable or unstable.

Plaques which form in the coronaries and other vessels comprise inflammatory cells, smooth muscles cells, cholesterol, and fatty substances, and these materials are usually trapped between the endothelium of the vessel and the underlying smooth muscle cells. Depending on various factors, including thickness, composition, and size of the deposited materials, the plaques can be characterized as stable or unstable. The plaque is normally covered by an endothelial layer. When the endothelial layer is disrupted, the ruptured plaque releases highly thrombogenic constituent materials which are capable of activating the clotting cascade and inducing rapid and substantial coronary thrombosis. Such rupture of an unstable plaque and the resulting thrombus formation can cause unstable angina chest pain, acute myocardial infarction (heart attack), sudden coronary death, and stroke. It has recently been proposed that plaque instability, rather than the degree of plaque build-up, should be the primary determining factor for treatment selection.

A variety of approaches for distinguishing stable and unstable plaque in patients have been proposed. Some of the proposals involve detecting a slightly elevated temperature within unstable plaque resulting from inflammation. Other techniques involve exposure of the plaque to infrared light. It has also been proposed to introduce radio labeled materials which have been shown by autoradiography to bind to stable and unstable plaque in different ways. External detection of the radiolabels, however, has limited the sensitivity of these techniques and makes it difficult to determine the precise locations of the affected regions. It would therefore be of great benefit to provide for improved radiolabels, compositions, and protocols for detecting vulnerable plaque and other inflammatory luminal conditions.

Once vulnerable plaque has been detected, it would be of significant benefit to provide methods for treating that plaque to reduce the risk of rupture and abrupt closure. Conventional intravascular treatments for stenotic lesions, such as angioplasty, atherectomy, and stenting may have only limited value in treating vulnerable plaques and in some instances might actually induce acute thrombosis at the site of the vulnerable plaque. Thus, it would be desirable to provide methods and compositions for treating vulnerable plaque to lessen the risk of rupture and abrupt closure.

2. Description of the Background Art

U.S. Pat. Nos. 6,197,278; 6,171,577 and 5,968,477 describe the preparation of radio labeled annexins and their use for imaging thrombus in the vasculature. U.S. 2003/0152513A1 suggests the delivery of conversion electrons for imaging vulnerable plaque. Stratton et al. (1995) Circulation 92:3113-3121, considers the use of radio labeled annexin V for intra-arterial thrombus detection. The use of radio labeled agents for detecting atherosclerotic lesions is described in the medical literature. See, for example, Elmaleh et al. (1998) Proc. Natl. Acad. Sci. USA 95:691-695; Vallabhajosula and Fuster (1997) J. Nucl. Med. 38:1788-1796); Demos et al. (1997) J. Pharm. Sci. 86:167-171; Narula et al. (1995) Circulation 92: 474-484; and Lees et al. (1998) Arteriosclerosis 8:461-470. U.S. Pat. No. 4,660,563, describes the injection of radio labeled lipoproteins into a patient where the lipoproteins are taken up into regions of arteriosclerotic lesions to permit early detection of those lesions using an external scintillation counter. U.S. Pat. No. 5,811,814, describes and intravascular radiation-detecting catheter. The catheter is used to locate tagged red blood cells that may accumulate, for example, in an aneurysm. U.S. Pat. No. 5,429,133, describes a laparoscopic probe for detecting radiation concentrated in solid tissue tumors. Miniature and flexible radiation detectors intended for medical use are produced by Intra-Medical LLC, Santa Monica, Calif. (www.intra-medical.com). See also U.S. Pat. Nos. 4,647,445; 4,877,599; 4,937,067; 5,510,466; 5,711,931; 5,726,153; and WO 89/10760.

The following publications some of which are referenced above are also pertinent:

1. Carnemolla B, Neri D, Castellani P, Leprini A, Neri G, Pini A, Winter G, Zardi L. Phage antibodies with pan-species recognition of the oncofoetal angiogenesis marker fibronectin ED-B domain. Int J Cancer. 1996; 68:397-405.
2. Neri D, Carnemolla B, Nissim A, Leprini A, Querze G, Balza E, Pini A, Tarli L, Halin C, Neri P, Zardi L, Winter G. Targeting by affinity-matured recombinant antibody fragments of an angiogenesis associated fibronectin isoform. Nat Biotechnol. 1997; 15:1271-1275.
3. Pini A, Viti F, Santucci A, Carnemolla B, Zardi L, Neri P, Neri D. Design and use of a phage display library. Human antibodies with subnanomolar affinity against a marker of angiogenesis eluted from a two-dimensional gel. J Biol Chem. 1998; 273:21769-21776.
4. Burrone J, Lagnado L. Electrical resonance and Ca2+ influx in the synaptic terminal of depolarizing bipolar cells from the goldfish retina. J Physiol. 1997; 505:571-584.
5. Viti F, Tarli L, Giovannoni L, Zardi L, Neri D. Increased binding affinity and valence of recombinant antibody fragments lead to improved targeting of tumoral angiogenesis. Cancer Res. 1999; 59:347-352.
6. Matter C M, Schuler P K, Alessi P, Meier P, Ricci R, Zhang D, Halin C, Castellani P, Zardi L, Hofer C K, Montani M, Neri D, Luscher T F. Molecular imaging of atherosclerotic plaques using a human antibody against the extra-domain B of fibronectin. Circ Res. 2004; 95:1225-1233.
7. Dinkelborg L M, Duda S H, Hanke H, Tepe G, Hilger C S, Semmler W. Molecular imaging of atherosclerosis using a technetium-99m-labeled endothelin derivative. J Nucl Med. 1998; 39:1819-1822.
8. Kolodgie F D, Petrov A, Virmani R, Narula N, Verjans J W, Weber D K, Hartung D, Steinmetz N, Vanderheyden J L, Vannan M A, Gold H K, Reutelingsperger C P, Hofstra L, Narula J. Targeting of apoptotic macrophages and experimental atheroma with radio labeled annexin V: a technique with potential for noninvasive imaging of vulnerable plaque. Circulation. 2003; 108:3134-3139.
9. Winter P M, Morawski A M, Caruthers S D, Fuhrhop R W, Zhang H, Williams T A, Allen J S, Lacy E K, Robertson J D, Lanza G M, Wickline S A. Molecular imaging of angiogenesis in early-stage atherosclerosis with alpha(v)beta3-integrin-targeted nanoparticles. Circulation. 2003; 108:2270-2274.
10. Halin C, Rondini S, Nilsson F, Berndt A, Kosmehl H, Zardi L, Neri D. Enhancement of the antitumor activity of interleukin-12 by targeted delivery to neovasculature. Nat Biotechnol. 2002; 20:264-269.
11. Halin C, Niesner U, Villani M E, Zardi L, Neri D. Tumor-targeting properties of antibody-vascular endothelial growth factor fusion proteins. Int J Cancer. 2002; 102:109-116.
12. Nilsson F, Kosmehl H, Zardi L, Neri D. Targeting delivery of tissue factor to the ED-B domain of fibronectin, a marker of angiogenesis, mediates the infarction of solid tumors in mice. Cancer Res. 2001; 61:711-716.
13. Birchler M, Viti F, Zardi L, Spiess B, Neri D. Selective targeting and photocoagulation of ocular angiogenesis mediated by a phage-derived human antibody fragment. Nat Biotechnol. 1999; 17:984-988.
14. D'Arceuil H, et al. 99m Tc annexin V imaging of neonatal hypoxic brain injury. Stroke 2000; 31:71-75.
15. Narula J, et al. Transient sarcolemmal phosphatidylserine expression as a marker of brief ischemia: An evaluation by 99m Tc-annexin V imaging. Journal of Nuclear Medicine 2000; 41:Suppl. p.173-174P.
16. Gidon-Jeangirard C, et al Annexin V delays apoptosis while exerting an external constraint preventing the release of CD4+ and PrPc+ membrane particles in a human T lymphocyte model. Journal of Immunology 1999; 162:5712-5718.
17. Gidon-Jeangirard C, et al Annexin V counteracts apoptosis while inducing Ca(2+) influx in human lymphocytic cells. Biochem *Biophys Res Commun*. 1999; 265:709-715.
18. Russo-Marie F. Annexin V and phospholipid metabolism. *Clin Chem Lab Med* 1999; 37:287-291.
19. Zwaal R F A, Schroit A J. Pathophysiologic implications of membrane phospholipid asymmetry in blood cells. *Blood* 1997; 89:1121-1132.
20. Fadok V A, et al. A receptor for phosphatidylserine specific clearance of apoptotic cells. *Nature* 2000; 405:85-90.
21. Hammill A K, et al Annexin V staining due to loss of membrane symmetry can be reversible and precede commitment to apoptotic death. *Exp Cell Res*. 1999; 251:16-21.
22. Strauss H W, et al. Radioimaging to identify myocardial death and probably injury. Lancet 2000; 356:180.

BRIEF SUMMARY OF THE INVENTION

The present invention provides compositions, apparatus, and methods for treating and/or imaging regions of vulnerable plaque and other inflammatory conditions within a blood vessel or other body lumen of a patient. While the invention is particularly intended for treating vulnerable plaque within a patient's vascular system, particularly the arterial system, including the coronary, peripheral, and cerebral arterial systems, it will be appreciated that at least certain aspects of the invention will be useful for treating other inflammatory conditions in addition to vulnerable plaque and treating body lumens and other target sites in addition to the vasculature.

Vulnerable plaque and other inflammatory conditions are treated by administering a conversion electron emitting source (CEES) to a patient. The CEES is preferably tin-117 m, but can also be holmium-166, thallium-201, technetium-99m, or the like. For therapeutic purposes, the CEES will be administered at a dose sufficient to inhibit rupture of vulnerable plaque, and/or treat vulnerable plaque which has ruptured typically at a total dosage range from 0.05 microcuries to 2 millicuries, more preferably in the range from 0.5 microcuries to 1 microcurie. For imaging, the CEES will be delivered under conditions which allow it to localize at a region of vulnerable plaque or other inflammatory response, and imaging will be based on external or other detection of emitted gamma radiation.

In one aspect of therapeutic treatment, the CEES will be bound to a substance that preferentially binds to or within the plaque, typically to markers of inflammation. Preferred binding substances may comprise any of those listed in Table 1 hereinafter. Alternatively, therapeutic methods may rely on administering the CEES via various devices and implants, such as intravascular catheters and other intraluminal probes, implantable scaffolds, such as stents, grafts, and the like.

Compositions according to the present invention will comprise a preferential binding substance, typically binding to a marker of inflammation or other molecular component associated with vulnerable plaque or other inflammatory responses, and a conversion electron emitting source, preferably tin-117 m or one of the other CEES's listed above. The preferential binding substance may be any of those substances listed in Table 1 hereinafter. The compositions will be prepared from irradiated tin-177 metal producing tin-177m having a specific activity for administration to a patient that provides a therapeutically effective emission in the range from 1 mCi/mg to 800 mCi/mg, preferably being about 21 mCi/mg.

These compositions are suitable for both therapeutic treatment and imaging of vulnerable plaque according to the methods described above.

The present invention may further comprise articles, devices, and other substrates which are coated with, coupled to, or otherwise associated with a CEES which are useful for treating vulnerable plaque and other inflammatory conditions in accordance with the methods of the present invention.

DETAILED DESCRIPTION OF THE INVENTION

The present invention provides for the administration of conversion electron emitting sources (CEES) to patients for therapeutic and diagnostic purposes. The CEES's will be modified or configured to enhance localization at regions of vulnerable plaque or other inflammatory regions. Pharmaceutical therapeutic compositions according to the present invention can be administered to any patient, including humans and animals, by parenteral, systemic, or local injections into vasculature or other locations, including the epidural, the subarachnoid compartment, solid tissue, the pulmonary system, the reticuloendothelial system, potential cavities, and the like. The compositions and methods will be suitable for imaging atherosclerotic atheroma, commonly referred to as hard plaque, as well as soft or vulnerable plaque, although treatment will be particularly effective for the soft or vulnerable plaque.

Imaging will rely on the detection of gamma photon emission from the CEES's. The imaging will typically be external, e.g. using a detector placed on or over the patient's skin or over a target body organ, but could in some places be local, e.g. using a catheter or other intravascular, intraluminal, or tissue-penetrating probe.

The CEES is preferably tin-117 m which primarily emits conversion electrons, but in some cases could also be holmium-166, thallium-201, or technetium-99m which have lesser conversion electron emissions. The tin-117 m will preferably be in metallic form and can be prepared in an accelerator, such as a linear accelerator or a cyclotron, by, for example, transmutation of antimony into known No-Carrier-Added tin-117 m by intermediate to high energy proton induced reactions. Alternatively, thermal or fast neutron bombardment of tin-117m or several other elements, using uranium-235, uranium-233, or plutonium-239, can be performed in a reactor to produce tin-117 m. The production of tin-117 m is well known in the art and does not form part of the present invention.

In the compositions of the present invention, the tin-117 m or other CEES is coupled, attached, or otherwise bound to a substance which preferentially or specifically binds to a component at a vulnerable plaque or other inflammatory site for diagnostic or therapeutic purposes. Suitable preferential binding substances are set forth in Table 1 below.

TABLE 1 a. Monoclonal Antibodies
   anti-ED-B human monoclonal antibodies
   monomeric scFv (single-chain Fv) antibody fragment
   noncovalent homodimeric scFv fragment
   miniantibody (small immune protein [SIP] in which the scFv moiety is fused to a
   CH4 domain of a human IgE serving as dimerization domain
   IgG - antibody to scavenger receptor (VLDL receptor)
b. Matrix Metalloproteinase-1, MMP-1
c. stromelysin (MMP-3)
d. MMP-8
e. gelatinases (MMP-2 and -9)
f. MMP-1, MMP-2, MMP-3, MMP-7, MMP-9, MMP-13 and tissue inhibitors of MMPs
   (TIMPs) TIMP-1 and TIMP-2
g. fibro-fatty plaque monocyte recruitment factor, smooth muscle cell migration and
   proliferation factor, and $CD4^+$ T cells
h. TM7 chemokine receptor CCR2
i. CC chemokines such as MCP-3
j. MCP-1-CCR2 ligand-receptor combination
k. CXC-inducible protein 10 (IP-10), monokine chemokine ligands including IFN-(Mig)
   and IFN-inducible T-cell alpha-chemoattractant (I-TAC) induced by IFN-
l. extra-domain B (ED-B) of fibronectin (91-aa domain)
m. human antibody L19 (specific against ED-B)
n. endothelin
o. annexin V
p. nanoparticles coated with anti-alpha v beta3 integrin peptidomimetic
q. fusion proteins with cytokines
r. vascular endothelial growth factor
s. procoagulant factors
t. conjugates with photosensitizers
u. Monocyte and Macrophage
   First stage:
   CFU-M: CD13, CD15, CD33, CD111, CD112, CD115, CD116, CDw123, and
   CDw131
   Second stage:
   Promonocyte: CD13, CD14, CD33, CD111, CD112, CD115, CD116, CDw123,
   and CD131
   Third stage:
   Monocyte: CD9, CD11b, CD11c, CDw12, CD13, CD14, CD15, CDw17, CD32,
   CD33, CD35, CD36, CD38, CD43, CD49b, Cd49e, CD49f, CD63, CD64, CD65s,
   CD68, CD84, CD85, CD86, CD87, CD89, CD91, CDw92, CD93, CD98, CD101,
   CD102, CD111, CD112, CD115, CD116, CD119, CDw121b, CDw123, CD127,
   CD128b, CDw131, CD147, CD155, CD156a, CD157, CD162, CD163, CD164,
   CD168, CD171, CD172a, CD172b, CD180, CD184, CD191, CD192, CD195,
   CDw198, CD206, CDw210, CD213a1, CD213a2, CD226, CD277, CD281,
   CD282, CD300a, CD300c, CD300e, CD302, CD305, CD312, CD317, CD322,
   CDw328, and CDw329.

TABLE 1-continued

Fourth Stage:
Macrophage: CD11c, CD14, CD16, CD26, CD31, CD32, CD36, CD45RO,
CD45RB, CD63, CD68, CD71, CD74, CD87, CD101, CD119, CD121b, CD155,
CD156a, CD204, Cd206, CDw210, and CD312.
End stage:
Activated macrophage: CD23, CD25, CD69, and CD105. (plus all the markers
expressed on macrophage).
v. Others:
CD31, ICAM1, VCAM, CD90, endoglin, VE-cadherin, integrin subunit a5 and b2,
CD44, and vimentin, Macrophage migration inhibitory factor (MIF), Direct conjugation
tin-117m to beta-VLDL particle or its associated lipoprotein or to oxidized LDL
particles.

Methods for inhibiting inflammation in hyperplasia in body lumens and other body target sites comprise delivering or implanting a CEES, preferably attached to one of the preferential binding substances listed above, to or within the body lumen or other body site. Methods are particularly useful for treating vulnerable plaque in the vasculature, as discussed above. Hyperplasia and inflammation, however, can also affect other body lumens, including the ureter, urethra, arterial venous dialysis shunts, the vaginal canal, the cervical os, the esophagus, the trachea, the bronchioles, the bronchi, and gastrointestinal tract, ostomies, biliary and pancreatic ducts, and the like.

The source of conversion electrons may be any of the CEES's described above. In co-pending U.S. patent application Ser. No. 60/652,129, a scaffold or other suitable luminal prosthesis tin-117 m on stent struts is described which could be used in the methods of the present invention. The CEES can be adapted for vulnerable plaque specific treatment devices that can be used for both imaging and/or therapy of vulnerable plaque. The CEES emitting molecule on a non-scaffolding luminal sheath with a metal tubing, foil or wire tubular configuration can be adapted to provide a therapeutically effective radiation emission and the non-scaffolding would not prop open or put significant outward pressure against the inner wall of the vessel. The radiation would typically be in the range from 0.0125 mCi/mm to 150 mCi/mm, usually in the range from 0.125 mCi/mm to 0.75 mCi/mm, especially for the combination of anti-inflammatory effect and tissue proliferation suppression. Because the therapeutic use of the non-scaffolding device may include non-tissue damaging suppression of the inflammatory reaction in a vessel or body lumen, dosimetry for radiation delivery can also be in the following range: 20 microCi [low], 60 microCi [medium], 120 microCi [high] per 20 mm length non-scaffolding sheath (i.e. 1 microCi/mm, 3 microCi/mm, 6 microCi/mm). A 20 mm length non-scaffolding sheath is used as an example and, of course, the radiation dose per mm length of non-scaffolding sheath would apply to shorter non-scaffolding sheaths. Other ranges that may be used include: 2.0 microCi [low], 6.0 microCi [medium], 12.0 microCi [high] per 20 mm length non-scaffolding sheaths (i.e. 0.1 microCi/mm, 0.3 microCi/mm, 0.6 microCi/mm). Higher therapeutic radiation levels than those disclosed above include:120 microCi [low], 240 microCi [medium], 480 microCi [high], 2500 microCi [very high] per 20 mm length stent (i.e. 6 microCi/mm, 12 microCi/mm, 24 microCi/mm, 125 microCi/mm). Implantation may comprise expanding the non-scaffolding tubular or other configuration CEES within the vessel or other body lumen, and specific CEES materials may be any of those described above. The half-life (t1/2) of tin-117 m is 14 days and the effective therapeutic time is 28 days or equal to two half-lives.

The storage time for the CEES in or on the non-scaffolding intravascular and intralumen device (NIID) can be increased by either increasing the purity of the tin-117 m/mg or by increasing the electroplating, electrodeposition or other method of adhering the tin-117 m to the NIID or platform to allow for the radioactive decay. Monthly preparation and distribution of NIID batches to cardiovascular use-centers, such as hospitals or local distribution centers, is possible. Each NIID batch would have a 3 to 5 day window-of-use differential (quantitatively) of plated NIIDs and this will accomplish adequate availability of for NIID use so that shipping of NIID can be performed on a monthly or 2 week basis. For example, if a first NIID batch has a 5 day usability window from the time of delivery to the cardiovascular use-center until the time the NIID must be put into a human coronary artery, this NIID would have a set mCi/mm and mCi/mg level of radioactivity placed on it for calender days 1 through 5; for example usability days March 1 through 5. For a second NIID batch delivered on the first day of March but for use on days 6 though 10 of the month, the radioactivity level of plating or deposition would be that of first NIID batch plus the average decay for 5 days so that on day 6 of March, the NIID would have the same radioactivity as the first NIID batch on March 1. On March 1 a set of NIID for use on March 10 through March 15 would also be delivered but would have plating of levels of radioactivity of tin-117 m as that of the first NIID batch plus enough tin-117 m to compensate for 10 days of decay so that the third NIID batch would have the same radioactivity on day 10 of March as the first NIID batch has on day 1 of March. The fourth through sixth NIID batches would have proportionally larger amounts of tin-117 m deposited on them to equal the radioactivity as the first NIID batch for use on its first designated and approved day. In this example a total of six batches of NIID could be delivered on the first part of each month with each batch implantable for successive five day intervals during the month.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A therapeutic composition comprising:
   no carrier added tin-117 m present at a therapeutically effective dosage; and
   annexin V bound to the no carrier added tin-117 m and capable of binding to a marker of inflammation.

2. A therapeutic composition as in claim 1, providing a total dosage in a range from 0.5 µCi to 2 mCi.

3. A therapeutic composition as in claim 2, providing a total dosage in the range from 0.5 µCi to 1 mCi.

4. A therapeutic composition as in claim 1, wherein the bound annexin V is capable of binding to vulnerable plaque in a patient's vasculature.

5. A therapeutic composition as in claim 1, wherein the no carrier added tin-117 m is in metallic form.

* * * * *